US00RE40428E

(19) United States
(12) Reissued Patent
Keane et al.

(10) Patent Number: US RE40,428 E
(45) **Date of Reissued Patent: *Jul. 8, 2008**

(54) SYRINGE HAVING NEEDLE ISOLATION FEATURES

(75) Inventors: Paul Keane, Plymouth (GB); Paul Barkell, Plymouth (GB); Volker Niermann, Bound Brook, NJ (US) 08805; Sol Green, North Woodmere, NY (US)

(73) Assignee: Becton, Dickinson and Company, Franklin Lakes, NJ (US)

( * ) Notice: This patent is subject to a terminal disclaimer.

(21) Appl. No.: 10/807,555

(22) Filed: Mar. 23, 2004

Related U.S. Patent Documents

Reissue of:
(64) Patent No.: 6,491,667
Issued: Dec. 10, 2002
Appl. No.: 09/644,914
Filed: Aug. 24, 2000

U.S. Applications:
(60) Provisional application No. 60/151,877, filed on Aug. 31, 1999.

(51) Int. Cl.
*A16M 5/32* (2006.01)

(52) U.S. Cl. ..... 604/192; 604/181; 604/187
(58) Field of Classification Search ..... 604/192, 604/256, 181, 187, 533
See application file for complete search history.

(56) References Cited

U.S. PATENT DOCUMENTS 3,987,930 A * 10/1976 Fuson ..... 220/287
4,667,837 A * 5/1987 Vitello et al. ..... 215/228
4,931,044 A * 6/1990 Beiter ..... 604/248
4,940,154 A * 7/1990 Vollmar ..... 215/249
5,086,783 A * 2/1992 Macors et al. ..... 600/578
5,125,415 A * 6/1992 Bell ..... 600/579
5,135,496 A * 8/1992 Vetter et al. ..... 604/111
5,167,642 A * 12/1992 Fowles ..... 604/263
5,250,037 A * 10/1993 Bitdinger ..... 604/192
5,256,154 A * 10/1993 Liebert et al. ..... 604/199
5,382,242 A * 1/1995 Horton et al. ..... 604/256
5,385,372 A * 1/1995 Utterberg ..... 285/332
5,390,898 A * 2/1995 Smedley et al. ..... 251/149.6
5,533,980 A * 7/1996 Sweeney et al. ..... 604/192
5,562,639 A * 10/1996 Lynn et al. ..... 604/523
5,624,402 A * 4/1997 Imbert ..... 604/111
5,685,845 A * 11/1997 Grimard ..... 604/82
5,718,690 A * 2/1998 Gettig ..... 604/232
5,741,236 A * 4/1998 Kakiuti ..... 604/192
6,027,482 A * 2/2000 Imbert ..... 604/256
6,126,640 A * 10/2000 Tucker et al. ..... 604/187
6,193,688 B1 * 2/2001 Balestracci et al. ..... 604/111
6,196,998 B1 * 3/2001 Jansen et al. ..... 604/111
6,206,861 B1 * 3/2001 Mayer ..... 604/246
6,394,983 B1 * 5/2002 Mayoral et al. ..... 604/192
6,632,199 B1 * 10/2003 Tucker et al. ..... 604/192

* cited by examiner

*Primary Examiner*—William E. Tapolcai
(74) *Attorney, Agent, or Firm*—Mark J. Schildkraut

(57) ABSTRACT

The present invention is a syringe tip cap comprising a bottom portion, a top portion, an annular skirt extending therebetween and a plug that projects proximally from the bottom portion so as to be telescoped into the passage of a syringe tip. The plug provides means to allow air to be vented from the syringe with contacting the user. The syringe tip cap of the present invention also provides the user with an indication by tactile and visual feedback that the syringe has been vented.

57 Claims, 4 Drawing Sheets

SYRINGE HAVING NEEDLE ISOLATION FEATURES

Matter enclosed in heavy brackets [ ] appears in the original patent but forms no part of this reissue specification; matter printed in italics indicates the additions made by reissue.

This application claims priority from provisional application No. 60/151,877, filed Aug. 31, 1999.

BACKGROUND OF THE INVENTION

1. Field of the Invention

The present invention relates to a syringe tip cap for use in blood collection and transport procedures and more particularly to a syringe tip cap for use with an arterial blood-sampling syringe or whole blood collection syringe.

2. Description of Related Art

Arterial blood samples are commonly obtained from a patient by using an arterial blood gas syringe or a whole blood collection syringe for arterial blood gas or other analytical analysis.

In the field of arterial blood gas syringes, it is important to prevent exposure of a collected blood sample to the atmosphere and to allow for the removal of trapped gases from the syringe once sampling is effected.

Conventional arterial blood gas syringes include a syringe barrel, a syringe tip, a luer connection, a standard needle and a plunger rod with a piston member on the distal end thereof.

When the syringe is being used to draw a blood sample, the needle is conventionally removed after draw and the syringe tip covered by a cap to isolate the sample during storage and/or transportation. Various tip cap structures have been disclosed having features designed to protect both the sample and the technician during capping, transportation and storage. Venting of these prior art structures is performed by inverting the syringe (tip up), removing the cap and visualizing advancement of the blood sample through the tip consequent to pressure applied to the plunger in order to remove any air left in the syringe tip and then transport the sample to the site of analysis.

While recent advances have contributed to improved technician safety during venting, further improvements are needed, particularly for syringe assemblies intended for arterial blood gas analysis, where residual gas left in a syringe after sampling may interfere with the analysis as well as to protect the user from exposure to the blood sample.

SUMMARY OF THE INVENTION

The present invention is a tip cap for use with an arterial blood gas syringe or whole blood collection syringe. Desirably, the syringe comprises a barrel, a syringe tip, a luer connection, a needle and a plunger rod with a piston member on the distal end of the plunger rod. In instances where the syringe is used to draw a sample by an arterial line, then the needle is not included.

Preferably, the syringe may also include a suitable additive such as an anticoagulant.

The syringe tip is preferably a slightly tapered conical tip projecting from the distal end of the syringe barrel. A passage extends through the syringe tip and communicates with the syringe barrel. The luer connection projects from the distal end of the syringe barrel and coaxially surrounds the syringe tip.

The tip cap preferably comprises a bottom portion, a top portion, and an annular skirt extending from the top portion to the bottom portion having an inner surface and an outer surface. The bottom portion comprises an inner and an outer end wall. The top portion comprises a rim. The annular skirt defines a diameter greater than the outside diameter of the syringe barrel. The outer surface of the annular skirt may include ribs such as protrusions or flats to enhance handling and gripping of the tip cap by the user.

The cap further includes an inner plug that projects proximally from the bottom portion inner end wall and is dimensioned to be telescoped into the passage of the syringe tip of the syringe barrel. The plug provides means to allow air to be vented from the syringe with depression of the syringe plunger. In addition, the plug provides tactile means to the user to indicate that the syringe has been vented.

The tip cap further comprises an intermediate wall projecting proximally from the inner end wall of the bottom portion of the tip cap and is in spaced surrounding relationship to the plug.

Preferably, the intermediate wall comprises an outer surface that is substantially cylindrical and an inner surface that is defined by six intersecting planar surfaces whereby the inner surface of the intermediate wall is substantially a hexagonal cross-section.

Preferably, the hexagonal cross-sectional of the inner surface of the intermediate wall provides a frictional fit with the conically tapered tip of the syringe. In addition, the outer surface of the intermediate wall preferably comprises vertical interference strips that assist the user in locating the cap onto the syringe, and more particularly whereby the strips engage with the luer connection on the syringe. The strips are of varying lengths to provide tactile feel to the user whereby the increasing resistance between the strips and the luer connection indicates to the user that the tip cap is at various positions. Preferably, the strips are vertical and of varying lengths to identify the venting position. The first position is the venting position and the second position is the secured position or final position whereby the tip cap and the syringe are removably secured.

Additionally, the tip cap further comprises a generally cylindrical internal sealing ring extending from the inner surface of the annular skirt and the inner end wall of the bottom portion. The internal ring further comprises an inner wall surface and outer wall surface. Most preferably, the internal sealing ring is separated from the outer surface of the intermediate wall by a first annular space. In addition, there is a second annular space between the inner surface of the annular skirt and the inner wall surface of the internal sealing ring.

The inner wall surface of the internal sealing ring further comprises indentations or grooves. The indentations provide the means to relieve pressure that may be caused when the syringe tip is pushed into the tip cap. In addition, the indentations may substantially reduce blood leakage from the syringe when the capped syringe is stored in ice water.

In use, the user draws a blood sample from a patient into an arterial blood gas syringe via a needle or intravenous line. Then either the needle is removed from the syringe and placed in a sharps container or the syringe is removed from the IV line. Then the user urges the tip cap over the distal end of the syringe barrel, with a slight twisting motion, whereby the luer connection will cooperate with the strips of the intermediate wall whereby the cap will progressively screw onto the syringe via the cooperation between the luer connection the strips and the plug telescopes into the conical passage of the tip of the syringe barrel. Alternatively, the cap may also be pushed onto the syringe.

The strips provide two stopping points for connecting the tip cap and the syringe. The first stopping point occurs when the user feels the tactile stopping point of the strips. At this first point, a venting position has been reached whereby the user points the syringe tip with the cap upwardly and lightly tapping the syringe barrel to move air bubbles to the distal end of the syringe barrel. The user then gently depresses the plunger so that air bubbles contained within the blood sample will be expelled via the venting mechanism of the plug. When all of the trapped air is removed from the blood sample, a resistance to further depress the plunger will be experienced by the user due to the design of the plug.

The second stopping point occurs when the planar interior surface of the intermediate wall gradually is urged into tight engagement with the outer surface of the conically tapered tip as the tip cap is telescoped onto the syringe barrel. Thus, the plug achieves a sealing of the passage through the tip while the intermediate wall achieves a frictional retention.

Preferably, the cap engages onto at least two of the four thread strips. Thereafter, the cap engages with two more threads, positioned slightly further down. The increase from two to four threads indicates to the user an increase in resistance to turn and therefore indicating the venting position.

The cap and syringe may be separated in a reverse twist off manner by applying a rotational force to the cap. Most preferably, an upward rotational force is applied to the cap and a downwardly force applied to the syringe along the longitudinal axis.

An advantage of the tip cap of the present invention is that it provides the user with tactile feedback when venting of air from the blood sample in the syringe is substantially complete as well as to visually alert the user that venting is complete.

Still another advantage of the tip cap of the present invention is that there is visual tactile feedback to the user whereby the user can view the syringe tip in the tip cap.

Another advantage of the tip cap of the present invention is that the outer surface of the tip cap contains features to enhance handling and grip for the user.

A notable advantage of the tip cap of the present invention is that the internal ring surrounds the luer connection of the syringe, assists in preventing any residual blood sample in the syringe luer connection from leaking out of the tip cap and luer connection, most notably during storage in ice water.

Another advantage of the present invention is that inclusions of water in the tip cap escape through channels.

A further advantage of the present invention is that the tip cap has a LED light transmission feature due to the structure and materials of construction.

Advantages of the tip cap of the present invention further include the attributes of the intermediate wall and the plug: (i) the strips lock the tip cap into place and substantially prevent the tip cap from being inadvertently removed from the syringe tip; (ii) the strips lock the tip cap into place with the luer connection and prevent the tip cap from being removed laterally from the syringe; (iii) the strips allow ease of use whereby the tip cap is easily screwed or urged into place with the syringe; (iv) the strips and the plug allow the tip cap to be partially seated with the syringe so that the sample in the syringe can be vented; (v) the strips and the plug provide the tip cap to be removable locked with the syringe to prevent accidental detachment of the tip cap and the syringe; (vi) the plug provides the means to vent air from the sample in the syringe without contacting the user; and (vii) the plug allows the syringe to be sealed from the atmosphere.

DETAILED DESCRIPTION

Figure 1:
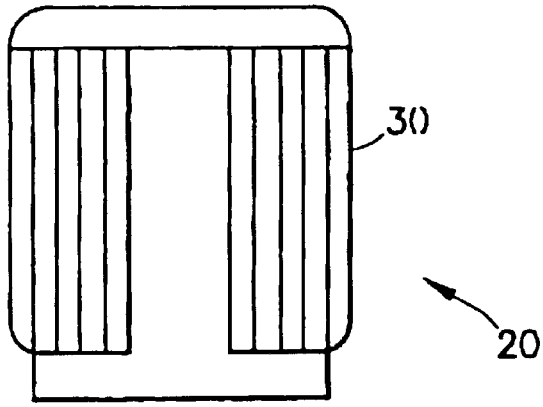
FIG. 1 is a perspective view of the tip cap of the present invention.
Figure 2:
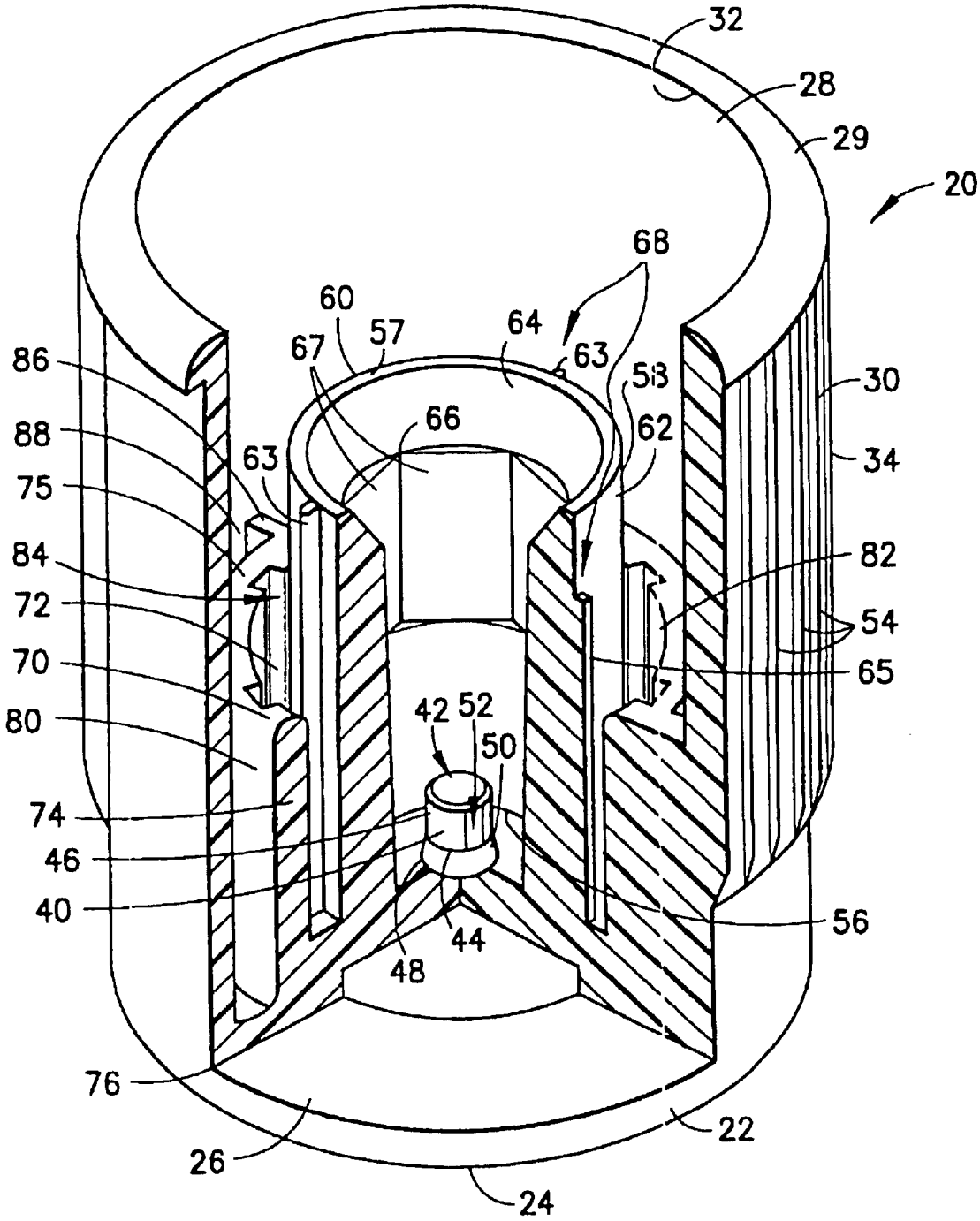
FIG. 2 is an enlarged cross sectional view of the cap of FIG. 1. taken along line 2—2 thereof.

Referring to the drawings in which like reference characters refer to like parts throughout the several views thereof, FIGS. 1 and 2 illustrate a tip cap 20 of the present invention.

Cap 20 as shown in FIGS. 1 and 2, has a closed bottom portion 22 having an outer end wall 24 and an inner end wall 26, a top open end 28 having a rim 29 and an annular outer skirt 30 extending from the closed bottom surface to the top open end. Annular skirt 30 includes an inner wall surface 32, an outer wall surface 34 and ribs, flats and/or protrusions 54 on the outer wall surface.

As shown in FIG. 2, tip cap 20 further includes a plug 40 that projects proximally from inner end wall 26 of closed bottom portion 22. Plug 40 is dimensioned to be telescoped into the passage of the syringe tip of a syringe barrel. Plug 40 includes a top end 42, a first end 44, a sidewall 46 extending between top end 42 and first end 44, a bottom end 48, a tapered sidewall 50 extending from first end 44 to bottom end 48 and a flat surface 52 extending vertically along sidewall 46.

As further shown in FIG. 2, a primary internal ring 60 projects proximally from inner end wall 26 and is in spaced surrounding relationship with plug 40. Primary internal ring 60 includes an outer surface 62, an inner surface 64, a bottom section 56, a top section 57, a sidewall 58 extending between bottom section 56 and top section 57. Outer surface 62 of primary internal ring 60 is substantially cylindrical and inner surface 64 is defined by a partial planar surface 66 that includes a plurality of planar surfaces 67 that form a substantially hexagonal cross-section.

Outer surface 62 of primary internal ring 60 further includes a plurality of vertical interference strips 68 of varying lengths, whereby interference strips 63 extend proximally from top section 57 downwardly on outer surface 62 and interference strips 65 extend proximally from bottom section 56 partially upwardly on outer surface 62 at a distance below strips 63.

As further shown in FIG. 2, a secondary internal ring 70 extends from inner wall surface 32 of annular skirt 30 and from inner end wall 26 of closed bottom portion 22. Secondary internal ring 70 is separated from outer surface 62 of primary internal ring 60 by a first annular space 72. Secondary internal ring 70 includes a top section 75, a bottom section 76 and a sidewall 74 extending from the top section to the bottom section. Sidewall 74 includes outer surface 80, inner surface 82 and indentations 84 on inner surface 82. Section compartments 88 are located between outer surface 80 and inner wall surface 32 of annular skirt 30, whereby the compartments are sectioned by sidewalls 86. Sidewalls 86 allow adequate molding conditions.

Figure 3:
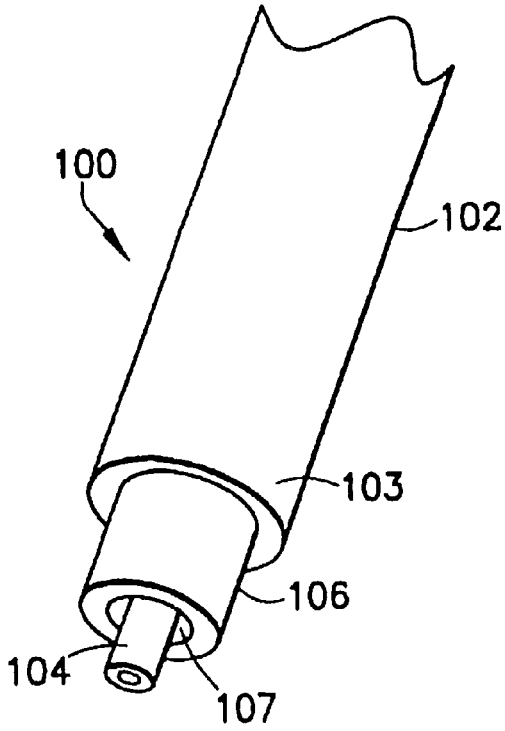
FIG. 3 is a perspective view of a syringe without the needle.

As shown in FIG. 3, syringe 100 includes a barrel 102 with a distal end 103, a syringe tip 104 and a luer connection 106 located at the distal end of the barrel with an annular space 107 between the syringe tip and the luer connection, a plunger rod 108 with a distal end 110 and a piston member 112 on the distal end of the plunger rod and a passageway 114 that extends through the syringe tip and into the barrel. Syringe tip 104 may be a slightly tapered conical tip.

Once a fluid sample is contained in syringe 100, tip cap 20 is removably secured to syringe 100. The tip cap is screwed onto the luer connection of the syringe whereby the luer connection progressively moves in communication with strips 63, plug 40 moves into communication with the conical tip of the syringe and the luer connection fits into first annular space 72. The movement of the tip cap stops at a first stopping point where the top strips terminate and before the bottom strips begin and at first end 44 of the plug. This first stopping point is easily felt by the user and indicates to the user that a venting position has been reached and that before the cap is removably secured to the syringe, the user should try and remove excess air bubbles from the fluid sample.

At this first stopping position, the user points the syringe tip with the tip cap upwardly whereby the user gently taps the barrel of the syringe to move air bubbles from the fluid sample to the tip of the syringe. The user then gently depresses the plunger so that air bubbles contained within the sample will be expelled through the tip cap via indents 52 of plug 40. When substantially all of the trapped air has been expelled, a resistance to further depress the plunger will be felt by the user, which is an indication that the syringe has been vented.

Then the user proceeds to continue screwing the cap fully onto the syringe, whereby the luer connection further cooperates with the bottom strips on the primary ring and the planar surfaces provide a friction fit with the conically tapered tip of the syringe, whereby the primary is gradually urged into tight engagement with the outer surface of the conically tapered tip. The plug achieves a scaling of the passageway through the tip, whereby the plug fits snugly in the passageway of the syringe tip and with bottom end 48 of the plug thereby indicating to the user that the tip cap is securely engaged with the syringe. The removably secured arrangement of the tip cap and the syringe is shown in FIGS. 4 and 5.

Figure 4:
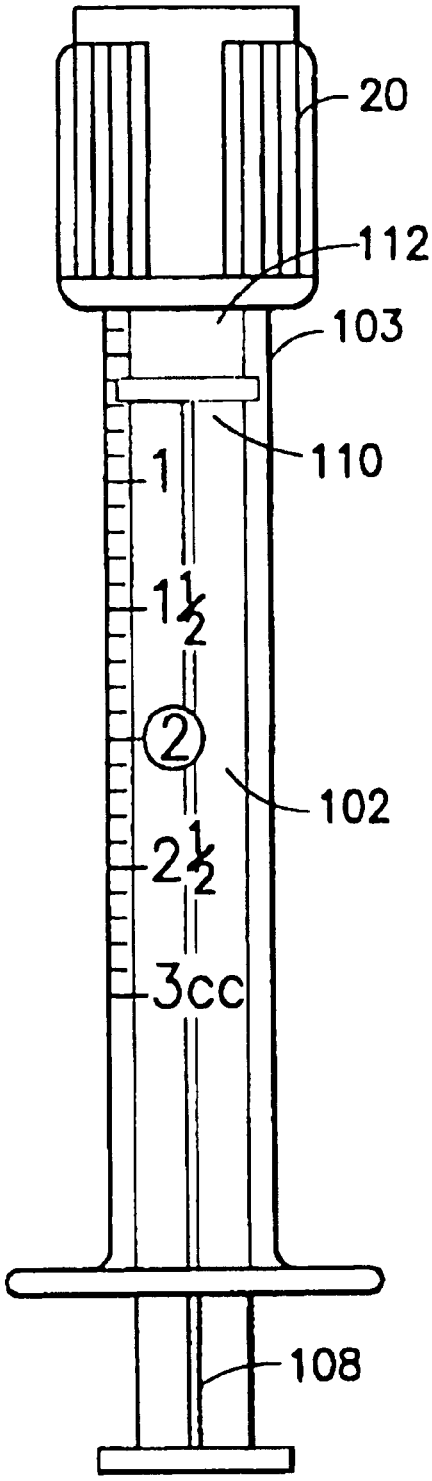
FIG. 4 is a perspective view of the syringe of FIG. 1 connected to the tip cap of FIG. 2.
Figure 5:
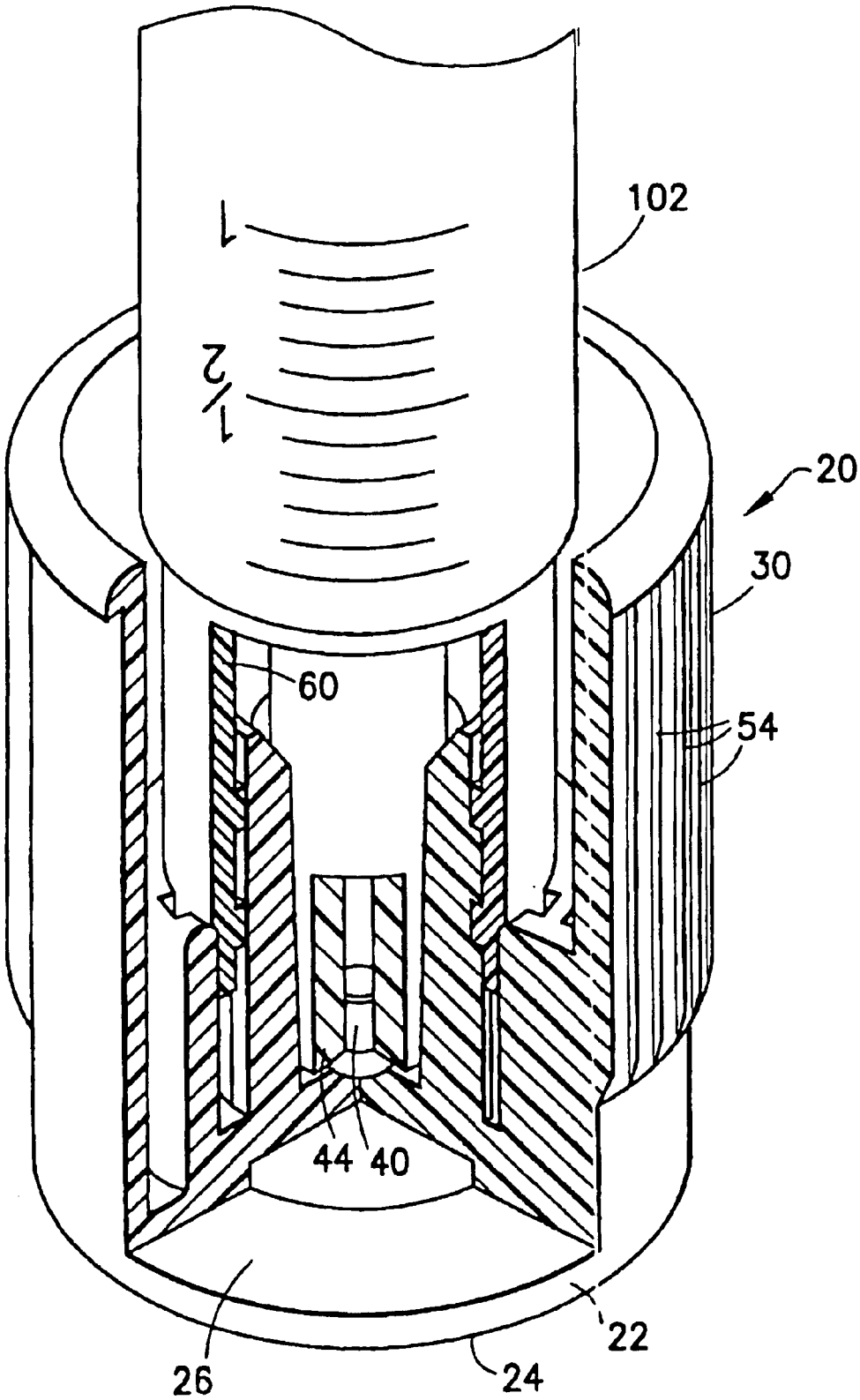
FIG. 5 is an enlarged elevational view, partially in section of the syringe and tip cap of FIG. 4, taken along line 5—5 thereof.

As shown in FIGS. 4 and 5, flats 54 are positioned on the outer wall surface of annular skirt 30. The flats substantially prevent the cap from rolling and provide a convenient grasping surface for ready removal and placement of the cap on the syringe. Although a smooth outer circumference without flats is within the purview of the instant invention, a cap with an outer surface with flats is preferred. In addition, outer end wall 24 of cap 20 is flat to allow the syringe when connected to the tip cap to be placed on a flat surface unattended, in an upright position thereby allowing ease of manipulation of the syringe by the user.

The tip cap of the invention may be made of a clear molded thermoplastic material so that the syringe tip may be readily viewed in the tip cap. Representative materials include, for example, polyethylene, polypropylene and polyvinyl chloride. Although it is within the purview of the invention to provide caps which are transparent, it is within the purview of this invention to provide caps which are color coded for defining the kind of examination to be conducted on the specimen collected.

The syringe may incorporate a hydrophilic material or a silicon may be applied to the internal surface thereof for enhancing the flow of blood introduced into the syringe.

What is claimed is:

1. A tip cap for sealingly covering the distal end of a syringe comprising:

a cylindrical housing having a bottom portion comprising an inner end wall and an outer end wall, a top portion comprising a rim and an annular skirt extending from said top portion to said bottom portion having an inner surface and an outer surface and means for venting air from said syringe and for providing tactile means to the user that said syringe has been vented by said tip cap.

2. The tip cap of claim 1, wherein said means for venting is an inner plug that projects proximally from said inner end wall of said bottom portion.

3. The tip cap of claim 2, further comprising an intermediate wall projecting proximally from said inner end wall of said bottom portion and spaced in surrounding relationship to said plug.

4. The tip cap of claim 3, wherein said intermediate wall comprises an outer surface that is substantially cylindrical and an inner surface that is defined by intersecting planar surfaces.

5. The tip cap of claim 4, wherein said inner surface of said intermediate wall is substantially a hexagonal cross-section.

6. The tip cap of claim 5, wherein said outer surface of said intermediate wall comprises vertical interference strips.

7. The tip cap of claim 6, wherein said interference strips comprise a first position to indicate a first venting position to the user and a second position to indicate to the user that said tip cap and said syringe are removably secure.

8. The tip cap of claim 7, further comprising a generally cylindrical internal sealing ring extending from said inner surface of said annular skirt and said inner end wall of said bottom portion.

9. The tip cap of claim 8, wherein said internal sealing ring comprises an inner wall surface and an outer wall surface.

10. The tip cap of claim 9, wherein said internal sealing ring is separated from said outer surface of said intermediate wall by a first annular space.

11. The tip cap of claim 10, further comprising a second annular space between said inner surface of said annular skirt and said inner wall surface of said internal sealing ring.

12. The tip cap of claim 11, further comprising indentations on said inner wall surface of said internal sealing ring.

13. A syringe assembly comprising:

a syringe comprising a barrel, a syringe tip, a luer connection, a needle and a plunger rod with a piston member on the distal end of said plunger rod; and a tip cap over said distal end of said syringe barrel comprising a cylindrical housing having a bottom portion comprising an inner end wall and an outer end wall, a top portion comprising a rim and an annular skirt extending from said top portion to said bottom portion having an inner surface and an outer surface and means for venting air from said syringe and for providing tactile means to the user that said syringe has been vented by said tip cap.

14. The assembly of claim 13, wherein said means for venting is an inner plug that projects proximally from said inner end wall of said bottom portion.

15. The assembly of claim 14, further comprising an intermediate wall projecting proximally from said inner end wall of said bottom portion and spaced in surrounding relationship to said plug.

16. The assembly of claim 15, wherein said intermediate wall comprises an outer surface that is substantially cylindrical and an inner surface that is defined by intersecting planar surfaces.

17. The assembly of claim 16, wherein said inner surface of said intermediate wall is substantially a hexagonal cross-section.

18. The assembly of claim 17, wherein said outer surface of said intermediate wall comprises vertical interference strips.

19. The assembly of claim 18, wherein said interference strips comprise a first position to indicate a first venting position to the user and a second position to indicate to the user that said tip cap and said syringe are removably secure.

20. The assembly of claim 19, further comprising a generally cylindrical internal sealing ring extending from said inner surface of said annular skirt and said inner end wall of said bottom portion.

21. The assembly of claim 20, wherein said internal sealing ring comprises an inner wall surface and an outer wall surface.

22. The assembly of claim 21, wherein said internal sealing ring is separated from said outer surface of said intermediate wall by a first annular space.

23. The assembly of claim 22, further comprising a second annular space between said inner surface of said annular skirt and said inner wall surface of said internal sealing ring.

24. The assembly of claim 23, further comprising indentations on said inner wall surface of said internal sealing ring.

*25. A tip cap for a syringe, comprising:*

*a housing comprising a bottom portion having an annular skirt extending therefrom, a first annular ring located within the skirt, and a second annular ring located within the first annular ring, wherein an annular space exists between at least a portion of the first annular ring and the second annular ring, and wherein the second annular ring or both the first annular ring and the second annular ring are capable of engaging a threaded luer connection.*

*26. The tip cap of claim 25, wherein a second annular space exits between at least a portion of the skirt and the first annular ring.*

*27. The tip cap of claim 26, wherein the second annular ring comprises an interior surface and an exterior surface, and wherein the exterior surface comprises at least two vertical strips.*

*28. The tip cap of claim 27, wherein the vertical strips are capable of engaging and providing securement to the threaded luer connection.*

*29. The tip cap of claim 28, wherein the vertical strips are deformable upon contact with the threaded luer connection, the deformation providing the securement to the threaded luer connection.*

*30. The tip cap of claim 25, wherein the first annular ring and the second annular ring extend from the bottom portion of the housing.*

*31. The tip cap of claim 25, wherein the annular gap between the first annular ring and the second annular ring is continuous.*

*32. The tip cap of claim 25, further comprising a vent located proximate the bottom portion of the housing, the vent located within the second annular ring.*

*33. The tip cap of claim 32, wherein the vent is integral with the bottom portion.*

*34. The tip cap of claim 32, wherein the vent is sized to fit into a syringe tip.*

*35. The tip cap of claim 32, wherein the vent is a solid plug.*

*36. The tip cap of claim 35, wherein the plug comprises a substantially circular, tapered outer wall having one or more flattened portions thereon.*

*37. The tip cap of claim 25, wherein an interior surface of the second annular ring comprises one or more planar portions.*

*38. A tip cap for a syringe, comprising:*

*a housing comprising a bottom portion having an annular skirt extending therefrom and an annular ring located within the skirt, the annular ring having an interior surface and an exterior surface, wherein the exterior surface comprises at least two vertical strips,*

*wherein the at least two vertical strips comprises a first strip of a first length and a second strip of a second length.*

*39. The tip cap of claim 38, wherein the vertical strips are capable of engaging and providing securement to a threaded luer connection.*

*40. The tip cap of claim 39, wherein the vertical strips are deformable upon contact with the threaded luer connection, the deformation providing the securement to the threaded luer connection.*

*41. The tip cap of claim 38, further comprising a vent located proximate the bottom portion of the housing, the vent located within the annular ring.*

*42. The tip cap of claim 41, wherein the vent is integral with the bottom portion.*

*43. The tip cap of claim 41, wherein the vent is sized to fit into a syringe tip.*

*44. The tip cap of claim 41, wherein the vent is a solid plug.*

*45. The tip cap of claim 44, wherein the plug comprises a substantially circular tapered outer wall having one or more flattened portions thereon.*

*46. The tip cap of claim 38, wherein an interior surface of the annular ring comprises one or more planar portions.*

*47. A tip cap designed for a syringe having a barrel, a syringe tip, and a luer connection at a distal end of the barrel, the tip cap comprising:*

*a housing comprising a bottom portion having an annular skirt extending therefrom and an annular ring located within the skirt, wherein the inner diameter of the skirt at the end of the skirt opposite the bottom portion is greater than the outer diameter of the syringe barrel.*

*48. The tip cap of claim 47, wherein upon physical engagement of the tip cap with the luer connection, the skirt extends proximally over the syringe such that the luer connection is contained within the interior of the housing.*

*49. The tip cap of claim 48, wherein upon engagement of the tip cap with the luer connection, the end of the skirt opposite the bottom portion surrounds a portion of the barrel.*

*50. The tip cap of claim 47, wherein an exterior surface of the annular ring comprises at least two vertical strips, and wherein the vertical strips are capable of engaging and providing securement to the threaded luer connection.*

*51. The tip cap of claim 50, wherein the vertical strips are deformable upon contact with the threaded luer connection, the deformation providing the securement to the threaded luer connection.*

*52. The tip cap of claim 47, further comprising a vent located proximate the bottom portion of the housing, the vent located within the annular ring.*

*53. The tip cap of claim 52, wherein the vent is integral with the bottom portion.*

*54. The tip cap of claim 52, wherein the vent is sized to fit into the syringe tip.*

*55. The tip cap of claim 52, wherein the vent is a solid plug.*

*56. The tip cap of claim 47, further comprising an intermediate annular ring located between the skirt and the*

*annular ring, wherein an annular space exists between at least a portion of the annular ring and the intermediate annular ring, and wherein the annular ring or both the annular ring and the intermediate annular ring are capable of engaging the threaded luer connection.*

*57. The tip cap of claim 56, wherein a second annular space exits between at least a portion of the skirt and the intermediate annular ring.*

* * * * *